(12) United States Patent
Friberg et al.

(10) Patent No.: US 6,775,001 B2
(45) Date of Patent: Aug. 10, 2004

(54) LASER-BASED SPECTROMETER FOR USE WITH PULSED AND UNSTABLE WAVELENGTH LASER SOURCES

(75) Inventors: Stephen R. Friberg, Mountain View, CA (US); Charles C. Harb, Pasadena, CA (US)

(73) Assignee: Lambda Control, Inc., Mountain View, CA (US)

( * ) Notice: Subject to any disclaimer, the term of this patent is extended or adjusted under 35 U.S.C. 154(b) by 0 days.

(21) Appl. No.: 10/377,976

(22) Filed: Feb. 28, 2003

(65) Prior Publication Data

US 2003/0218750 A1 Nov. 27, 2003

Related U.S. Application Data

(60) Provisional application No. 60/360,779, filed on Feb. 28, 2002.

(51) Int. Cl.[7] .............................................. G01N 21/00
(52) U.S. Cl. ....................... 356/437; 356/432; 356/433; 356/435
(58) Field of Search ................................ 356/432–442, 356/416–418; 250/343, 458.1, 459.1, 461.1, 461.2, 599.4, 339.13, 559.4, 573, 576, 345

(56) References Cited

U.S. PATENT DOCUMENTS

| | | | | |
|---|---|---|---|---|
| 3,790,798 A | * | 2/1974 | Sternberg et al. | 250/345 |
| 4,794,255 A | * | 12/1988 | Miyatake et al. | 250/343 |
| 4,823,354 A | * | 4/1989 | Znolins et al. | 372/57 |
| 5,173,749 A | * | 12/1992 | Tell et al. | 356/437 |
| 5,572,031 A | * | 11/1996 | Cooper et al. | 250/343 |
| 5,636,035 A | * | 6/1997 | Whittaker et al. | 356/437 |
| 5,930,000 A | * | 7/1999 | Brand | 356/437 |
| 6,040,915 A | * | 3/2000 | Wu et al. | 356/435 |
| 6,121,627 A | * | 9/2000 | Tulip | 250/559.4 |

* cited by examiner

*Primary Examiner*—Frank G. Font
*Assistant Examiner*—Sang H. Nguyen
(74) *Attorney, Agent, or Firm*—Dorsey & Whitney LLP

(57) ABSTRACT

A laser absorption spectrometer for making measurements of absorption spectra which includes a wavelength sensor that can measure the average wavelength of pulses from a laser on a pulse-by-pulse basis and that can measure the internal wavelength variation of laser pulses. The laser absorption spectrometer can be used with pulsed lasers like the quantum cascade laser to perform sensitive measurements of the absorption spectra even when there is pulse-to-pulse variation of average wavelength and when there are internal changes in the wavelength of the pulses.

12 Claims, 4 Drawing Sheets

LASER-BASED SPECTROMETER FOR USE WITH PULSED AND UNSTABLE WAVELENGTH LASER SOURCES

RELATED APPLICATIONS

This application claims priority to Provisional Application Serial No. 60/360,779 filed Feb. 28, 2002.

FIELD OF THE INVENTION

This invention relates generally to a laser-based spectrometer that is used to measure the absorption spectrum and other physical parameters of trace gases and other substances. Specifically, it provides a way to use room-temperature quantum cascade lasers and other pulsed and unstable wavelength laser sources for sensitive absorption measurements. This invention can be used in the field of laser spectroscopy, industrial processing, environmental monitoring, medicine, biophotonics, and related fields and in particular in the mid-infrared range (3 $\mu$m to 15 $\mu$m) with room-temperature quantum cascade lasers for spectroscopic measurements.

BACKGROUND OF THE INVENTION

Gaseous, solid, molecular, chemical, or biological substances can be identified and much information about their surrounding environment—temperature, pressure, neighboring material constituents, completed or ongoing chemical and biological activities, for example—can be obtained by measuring the optical spectrum of light that the substances emit or absorb. The making of such measurements is spectroscopy, a wide and diverse field with applications in industry, environmental monitoring, process control, research and development, combustion control, forensics, and a variety of other fields. Applied to biological tissues, materials, or molecules, spectroscopy is a component of biophotonics, a rapidly growing field embracing the life sciences and optical measurement technologies. Applied to medicine, spectroscopy is a component of the rapidly growing field of medical photonics.

Absorption spectroscopy, where the amount of light absorbed in a substance is determined at different wavelengths, is one of the most important of the spectroscopic measurements. Absorption measurements using narrowband tunable lasers having a bandwidth narrower than the absorption features of the substance to be measured have become particularly important, as they allow increased sensitivity and can be done with simple apparatus. In particular, they can be carried out without using monochromators or spectrometers that are otherwise required to provide narrowband optical signals or high resolutions. Furthermore, narrowband laser sources provide much more intense concentrations of light in the required measurement bandwidth, greatly increasing the ease of detection and reducing measurement times.

The sensitivity of an absorption measurement is determined by the absorption cross section of the substance to be measured at the measurement wavelength, by the distance the measurement beam travels through the medium containing the substance, and by the ability of the photodetection apparatus to detect small changes in power transmitted through the substance. Absorption cross sections are usually larger at longer wavelengths, so measurement sensitivities can be increased by operating in the mid-infrared wavelength region (3 $\mu$m to 15 $\mu$m) as opposed to the near-infrared wavelength region (0.8 $\mu$m to 3 $\mu$m) or the visible wavelength region (0.4 $\mu$m to 0.8 $\mu$m). For example, moisture can be detected at 2.0 parts per billion (ppb) sensitivity at 5.94 $\mu$m, but only 60 ppb sensitivity at 1.39 $\mu$m using typical measurement parameters. For some substances, the sensitivities are vastly different. For carbon dioxide, for example, the detection sensitivities are 0.13 ppb at 4.23 $\mu$m versus detection sensitivities of 3,000 ppb at 1.96 $\mu$m. For carbon monoxide, detection sensitivities are 0.75 ppb at 4.60 $\mu$m versus 30,000 ppb at 1.570 $\mu$m. These numbers show that measurement sensitivities can be a thousand or even ten thousand times more sensitive at mid-infrared wavelengths. A consequence is that measurements at longer wavelengths can be carried out using much shorter path lengths and lower detection efficiencies provided that appropriate lasers are available. This lowers costs considerably.

The usual method for carrying out a spectroscopic absorption measurement of the concentration of a trace gas or other substance using a laser is outlined in FIG. 1. Light from a semiconductor laser 11 is collimated into a parallel beam using collimator 12 consisting of a telescope and spatial filter. The collimated parallel beam of light propagates to beamsplitter 13 which sends part of the beam through lens 14 to photodetector 15 where it is detected and the resulting photocurrent sent to the electronics processor 16. The remainder of the collimated parallel beam propagates through gas cell 17 containing the gas or other substance to be measured. The gas cell may be a single pass cell where light passes through once, it may be a multi-pass cell where there are reflecting mirrors that reflect the beam back and forth several times, or the gas cell may be simply an area of free space that the beam passes through. After passing through the gas or other substance to be measured, the beam is focused through lens 18 onto photodetector 19 where it is detected and the resulting photocurrent sent to the electronics. FIG. 2 shows a representative absorption spectrum for nitric oxide calculated assuming a concentration of 1 part per billion, a pressure of 0.08 atm, and an absorbing path length of 5000 meters. FIG. 3 show details of the absorption spectrum of FIG. 2.

Spectroscopy, like many other photonics technologies, is moving out of the laboratory and into the workplace. The growth in the number of applications, combined with the advances in photonics achieved in the related field of optical telecommunications, has both increased the market size for spectroscopic devices and has created strong interest in the development of low-cost, small, easy to use, reliable, robust, and sensitive spectroscopic devices. In particular, the commercialization of tunable semiconductor lasers for optical telecommunications applications has lead to the ready availability of low-cost infrared laser sources that, combined with modern optical and electronics design, have the potential to open broad new markets for spectroscopic instruments. Infrared diode lasers offer the possibility of building spectroscopic absorption measurement devices that have increased sensitivity, including the capability to measure trace gas concentrations in the part per billion range; excellent selectivity for a particular substances without interference from other substances, robustness, maintenance-free operation, long laser lifetimes, speed, simple control and data acquisition mechanisms, small, compact designs, and low costs.

Semiconductor laser sources currently in use or under development in the near-infrared include inexpensive high-quality easily-tunable DFB and DBR lasers that operate at room temperature that are ideal for spectroscopic applications. In the mid-infrared where absorption cross sections are large and the potential for sensitive, low-cost devices is the greatest, the choices are lead-salt semiconductor lasers and unipolar quantum well lasers (quantum cascade lasers). However, lead-salt lasers require cryogenic cooling, have narrow tuning ranges, and have mode hops where the operating wavelength changes abruptly. Quantum cascade lasers have excellent properties when cooled to cryogenic temperatures, but operate at room temperature only in a pulsed mode that produces a sequence of pulses where the wavelength changes in time and the pulses vary in average wavelength. This rules out sensitive absorption measurements with lasers operating at room temperature using conventional measurement techniques in the mid-infrared.

Quantum cascade lasers, although not able to operate continuously at room temperature, are otherwise ideal for mid-infrared spectroscopic measurements in general and trace gas measurements in particular. They are fabricated from well-understood materials (for example, indium gallium arsenide and aluminum indium arsenide) and can operate at nearly all wavelengths between 3.5 $\mu$m and 24 $\mu$m. Single-mode operation with narrow line widths (100 kHz or smaller) is easily possible, and continuous tunability over tens of nanometers is achieved by adjusting drive currents. They are robust, reliable, and have good long-term stability. They have been shown to be capable of generating ultra-short pulses of 3 to 5 picosecond duration at high repetition rates and 50 picosecond pulse widths when gain-switched, opening up opportunities for time-resolved spectroscopy. However, for room-temperature operation, highly desirable if device costs are to be low, they have broadened spectral bandwidths due to thermal chirp and pulse-to-pulse wavelength variation, restricting their use in traditional absorption spectroscopy to a limited number of measurements involving very broad features of certain absorption spectra.

If a laser cannot operate continuously at room temperature, it is typically because heat generation combined with feedback mechanisms causes lasing instabilities that causes additional heat generation that turns the laser off. Pulsed operation, where the laser is turned on for and interval and then turned off for a longer interval, reduces heat generation and halts instabilities and allows room temperature operation. When laser drive currents are turned on and off quickly, as is the case for the gain-switching pulse operation of quantum-cascade lasers, then the laser operates in its turn-on mode only and steady-state narrowband operation is not achieved. Two problems then occur. One is that the laser wavelength changes rapidly as the laser starts to warm up and the lasing mode is established. The other is that the laser does not turn on in the same way for each pulse. The first results in what is called wavelength chirp and the second results in pulse-to-pulse average wavelength variations. Both processes are detrimental to laser spectroscopy as typical measurement processes cannot account for the fast time variation of the wavelength of the pulse, or cannot measure the pulse-to-pulse variation of the laser wavelength. Accordingly, a pulsed laser must be treated as if it were a laser with much broader bandwidth, limiting its use for trace gas measurements and other sensitive spectroscopic measurements.

One way to resolve the problem of pulse-to-pulse wavelength variations or wavelength chirped pulses is to use fast wavelength measuring devices that measure a pulse's instantaneous wavelength or measure its pulse-to-pulse average wavelength variation. Most commercial wavelength measuring devices are wavelength averaging devices and very slow, taking fractions of a second for a measurement. They are therefore not capable of following internal pulse wavelength variations on a fast time scale or measuring pulse average wavelengths at repetition rates faster than ten repetitions or so per second. Fast wavelength variations can be observed by heterodyne mixing processes where a laser with a fixed wavelength (the local oscillator) is mixed with the signal to be measured on the surface of a photodetector and the difference frequency components are recorded. Or, fast wavelength variations can be measured with a newly invented technique called frequency-resolved optical gating (FROG). This uses a combination of spectroscopic measurement techniques and short pulse autocorrelation processes to characterize the spectral characteristics of short pulses.

If the pulse-to-pulse wavelength variation is known along with the corresponding transmission information in an absorption spectroscopy experiment, or if the instantaneous wavelength information of a chirped pulse is known along with the corresponding transmission information, then measurement accuracies and trace gas measurement sensitivities can be improved. However the mechanisms for fast wavelength measurements described above are unwieldy, require substantial amounts of equipment, introduce considerable complexity into the measurement, increase equipment size, inflate costs, and have other limitations as well. Heterodyne mixing using a local-oscillator laser requires a laser that produces a narrowband continuous signal at or near the wavelength of interest, usually requiring cryogenic cooling at mid-infrared wavelengths. The local oscillator laser and pulsed laser signals mix in the measurement process to produce radio frequency signals at the wavelength difference. This introduces the need to measure the magnitude of the radio frequency signal and limits the range of wavelength differences that can be determined. If frequency-resolved optical gating techniques are used, then considerable complexity and considerable computation power is required, and the ability to follow high repetition rate sources is eliminated.

Another possible way to address the problem of laser pulses with substantial wavelength variation or random pulse-to-pulse wavelength variations is to perform a correlation measurement where a sample of the gas or substance to be measured is compared with the unknown gas or substance. FIG. 4 shows a schematic diagram of the measurement apparatus. Light from a laser or other source 11 is collimated into a beam by a collimator 12 and split into two beams with beamsplitter 13. One beam is transmitted through cell 17 that contains the gas or substance to be measured and focused with lens 18 onto photodetector 19. The other beam is reflected by mirror 20 and transmitted through a second cell 21 containing a known concentration of gas or the sample to be measured and focused through lens 22 onto a second photodetector 23. Photocurrents from each of the photodetectors are subtracted from each other at an electrical subtractor 24 to provide a signal that is a correlation of the absorption spectrum of the unknown sample and the known reference sample. The correlation signal can be used to detect the presence or absence of the substance in the reference cell when the source has a complicated and time varying spectrum of the sort that accompanies a chirped source or pulse-to-pulse variations. However, this method does not provide a method to determine the wavelength characteristics of the laser pulses.

OBJECTS AND ADVANTAGES OF THE INVENTION

It is an object of the present invention to provide an apparatus and method that overcomes many of the foregoing problems. Advantages of the present invention are that it provides a method to measure the average wavelength of the pulses from the laser source on a pulse-by-pulse basis and to combine that information with the measurement of the absorption of the light in the sample to obtain a narrow-band laser absorption measurement. The method makes it possible to use semiconductor lasers with pulsed room temperature operation for sensitive absorption spectroscopy measurement as individual pulses have narrower bandwidths than can be observed and recorded using traditional wavelength measurement means. Our present invention, by using wavelength sensing devices that are capable of very fast operation, also has the advantage that it can follow the wavelength variations of pulses that change in wavelength, thus effectively providing scanned wavelength measurements of features of a samples absorption spectrum.

Other objects and advantages of the present invention are:

a) to provide an apparatus for absorption spectroscopy measurements that can use quantum cascade semiconductor lasers operating at room temperature b) to provide an apparatus for absorption spectroscopy measurements that is inexpensive c) to provide an apparatus for absorption spectroscopy measurements that can be readily miniaturized, d) to provide an apparatus for absorption spectroscopy measurements that can use lasers with naturally occurring wavelength variations e) to provide an apparatus for absorption spectroscopy measurements that can do correlation spectroscopy measurements using pulsed laser and other lasers with naturally occurring wavelength variations in their output.

SUMMARY OF THE INVENTION

The objectives and advantages of the invention are achieved by an optical system that directs a collimated beam of light from a laser source down three predetermined paths, one proceeding through a sampling cell containing a sample medium whose absorption is to be measured followed by a photodetector, the second proceeding to a wavelength sensor capable of very fast operation described in U.S. patent application Ser. No. 09/954,086 incorporated herein in its entirety by reference, and the third proceeding to a monitor photodetector. Light proceeding through the sample cell is detected by a photodetector that provides photocurrents proportional to the light's intensity, light directed to the wavelength sensor produces a signal corresponding to the light's wavelength, and light detected by the monitor photodetector produces a photocurrent that is proportional to the intensity of light entering into the sample cell. A divider divides the sampling cell photodetector photocurrent by the monitor photodetector photocurrent to provide a measurement of the absorption of the sample material at the wavelength measured by the wavelength sensor. Varying the wavelength of the light from the laser either by natural or artificial means, an absorption spectrum measurement of the sample over the wavelength variation range can be obtained.

More particularly, the apparatus includes an optical system comprising lenses that collimate the light emerging from the laser source. The system may include a spatial filter to eliminate unwanted light. Two beamsplitters that direct light to a wavelength sensor and the monitor photodetector. A sampling cell that contains the material whose absorption spectrum is to be measured. Lenses couple the collimated light into the wavelength sensor and the photodetectors. The wavelength of the light from the laser source may be varied artificially by changing the laser's driving currents, its temperature, or by other means, or as is the case for many semiconductor lasers operated in pulsed mode, the wavelength of each pulse may vary naturally on a pulse-by-pulse basis. Absorption measurements obtained by dividing the sample cell photocurrent by the monitor photocurrent are paired with wavelength measurement numbers from the wavelength sensor and stored and processed electronically to build up a measurement of the absorption spectrum over the range of interest. Where the wavelength of the laser source can be artificially varied, the absorption spectrum might be obtained by scanning the wavelength over a suitable range. When a pulsed laser source with pulses that vary in average wavelength on a pulse-by-pulse basis is employed, the absorption spectrum is obtained by waiting for the wavelength range of interest to be covered by natural variations of the laser pulse wavelengths or by a combination of natural and artificial variations.

The electronics system may be comprised of one photodetector preamplifier for each of the photodetectors; electronics for the wavelength sensor, one logarithmic amplifier for each of the photodetected signals; and a difference amplifier for subtracting the two logarithmic signals followed by analog-to-digital converters and digital memory and processors, or by photodetector preamplifiers for each of the photodetectors, analog-to-digital converters for the each of the photodetectors, electronics for the wavelength sensor, and digital memory and processors.

BRIEF DESCRIPTION OF THE FIGURES

The present invention will be better understood by reading the following detailed description in conjunction with the accompanying drawings in which.

DETAILED DESCRIPTION OF THE INVENTION

Figure 5:
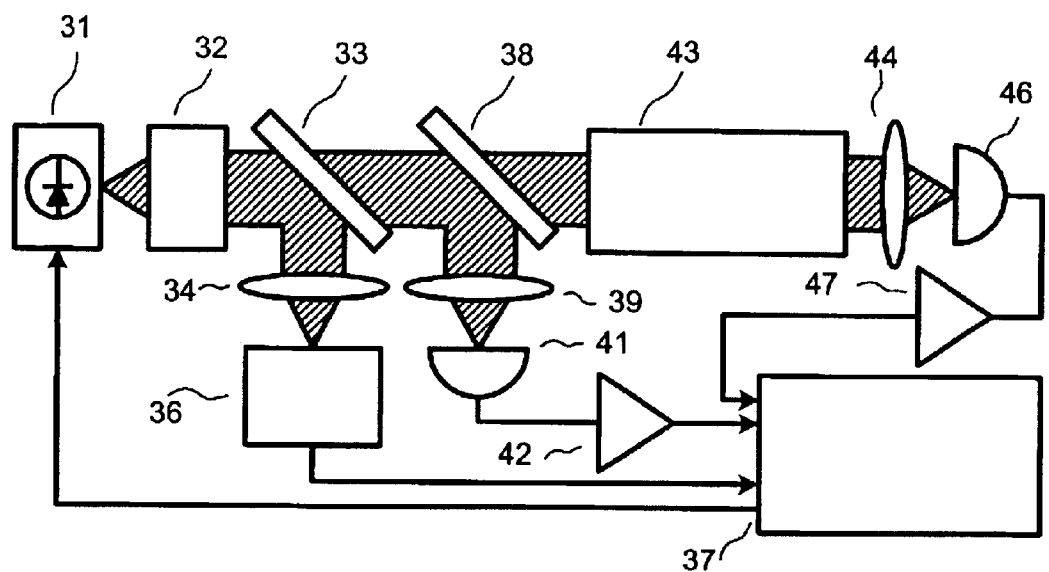
FIG. 5 is a schematic diagram of an absorption measurement device for measuring the absorption of a substance using light from a laser in accordance with an embodiment of the invention.

FIG. 5 shows the basic optical and electrical components of an absorption measurement by a system in accordance with one embodiment of the present invention. Light from laser 31 is collimated into a parallel beam using collimator 32 consisting of a telescope and spatial filter. The collimated parallel beam of light propagates to beamsplitter 33, which sends part of the beam through lens 34 to a wavelength sensor 36 system where the wavelength of the light from the laser is measured and the resulting measurement is sent to the electronics processor 37. A suitable rapid wavelength sensor is shown and described with reference to FIG. 6, other variations of the wavelength sensor are described in pending application Ser. No. 09/954,086 incorporated herein in its entirety. A rapid wavelength sensor can be purchased from Wavelength sensors are available by ordering from Lambda Control, Inc., 129 Concord Circle, Mountain View, Calif., 94040, Tel: 650-947-4805, E-mail: friberg@lamctrl.com. Part numbers are LC-WME-NP-B21-V01 for a wavelength sensor in a butterfly package with no electronics and LC-WLE-AP-B21-V010 for a wavelength sensor in a butterfly package with analog signal processing electronics.

The rest of the beam goes to a second beamsplitter 38 which sends a second part of the beam through lens 39 to a monitor photodetector 41 and the resulting photocurrent is amplified by amplifier 42 and sent to the electronics processor 37. The remainder of the collimated parallel beam propagates through gas cell 43 containing the gas or other substance to be measured. The gas cell may be a single pass cell where light passes through once, it may be a multi-pass cell where there are reflecting mirrors that reflect the beam back and forth several times, or the gas cell may be simply an area of free space that the beam passes through. After passing through the gas or other substance to be measured, the beam is focused through lens 44 onto photodetector 46 where it is detected and the resulting photocurrent is amplified by amplifier 47 and sent to the electronics processor 37.

Figure 6:
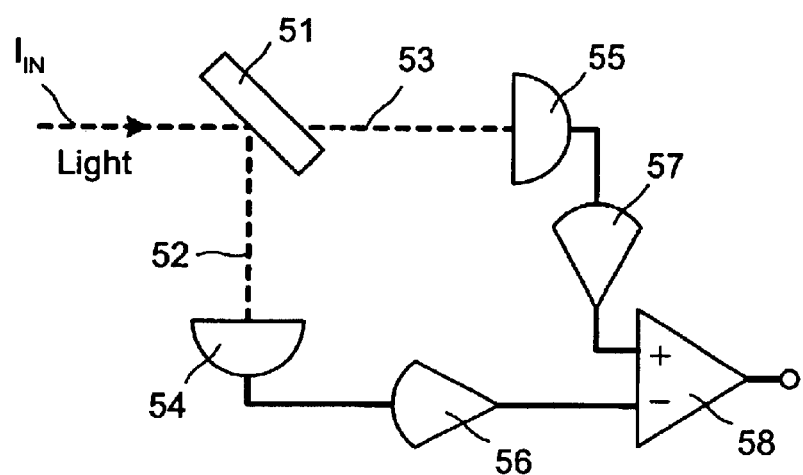
FIG. 6 is a schematic diagram of the wavelength sensor of FIG. 5.

FIG. 6 shows the basic optical and electrical components of a wavelength sensor that is one embodiment of pending application Ser. No. 09/954,086. The sensor is positioned to receive an optical signal (beam) $I_{IN}$. The detector includes a beamsplitter 51 whose transmission varies with wavelength to form two beams 52 and 53. The beams are received by photodetectors 54 and 55. Analog log-amplifier circuits 56 and 57 receive the output of the photodetectors and provide the log of the current received from the photodetectors. The two log outputs are subtracted by subtractor or difference amplifier 58 to provide a signal representative of wavelength of optical signal. This signal can then be used with a look-up table or the like to provide a measurement of wavelength.

The apparatus diagrammed in FIG. 5 and described in the paragraph above has two main modes of operation for use with semiconductor or other lasers that produced pulses with time-varying wavelengths (chirped pulses) or that have pulse-to-pulse wavelength variations. The first mode of operation is a-pulse by-pulse averaging mode where the average wavelength of the pulse and the accompanying measurement of the absorption in the sample cell are recorded as a pair. The second mode of operation is a fast real-time simultaneous measurement of the wavelength of the laser pulse and the absorption spectrum of the cell. Both modes rely on the property of the wavelength sensor of being able to make very fast measurements of the optical wavelengths.

Figure 1:
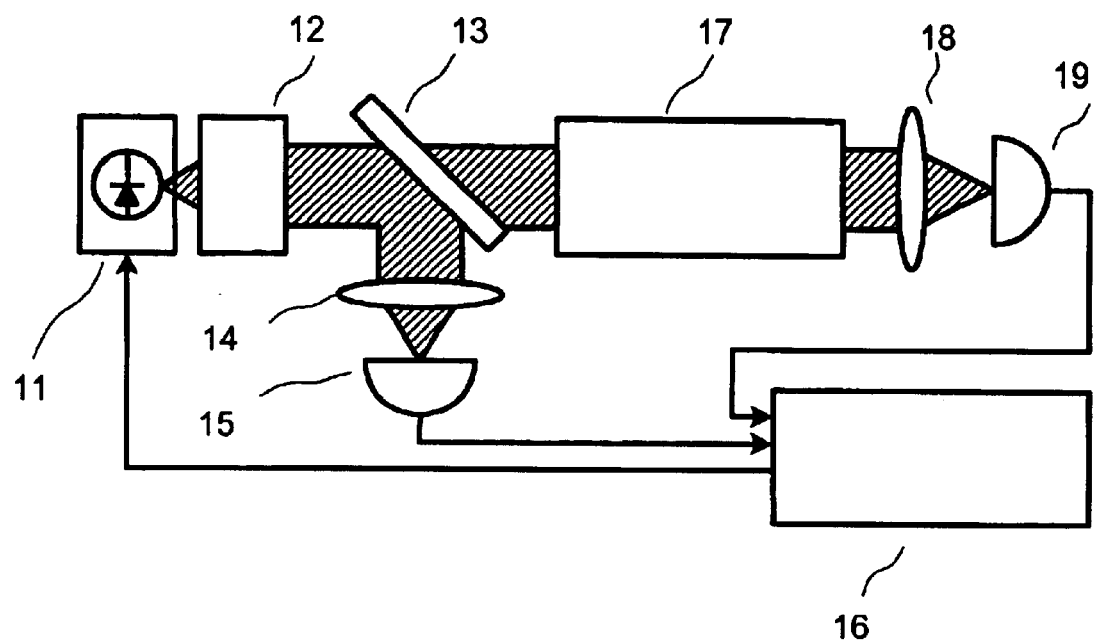
FIG. 1 is a schematic diagram of a prior art apparatus for measuring the absorption of a substance using light from a laser.
Figure 2:
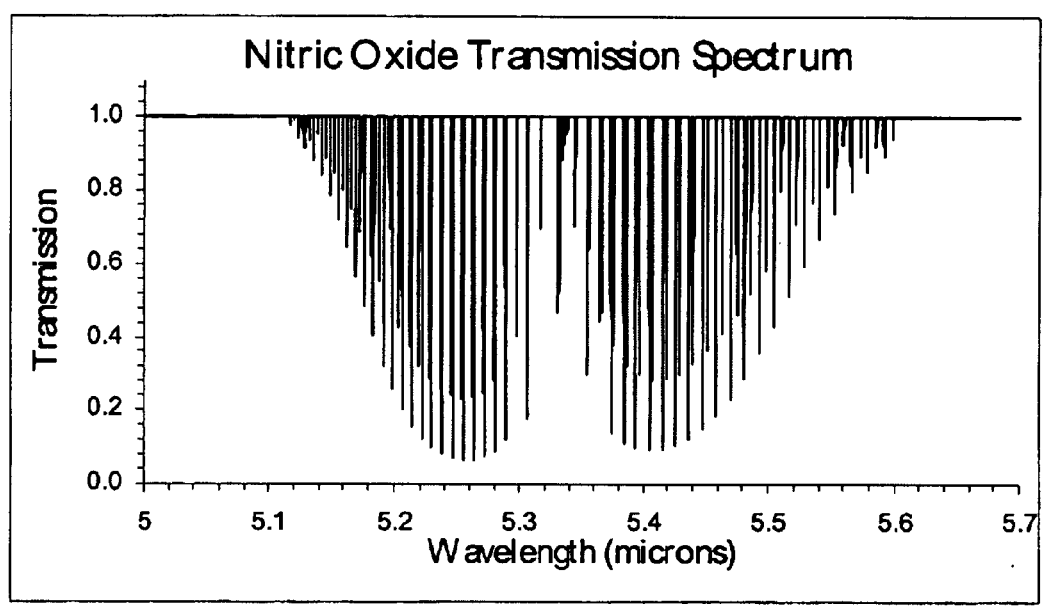
FIG. 2 shows an example absorption spectrum of the type that can be observed by the apparatus.
Figure 3:
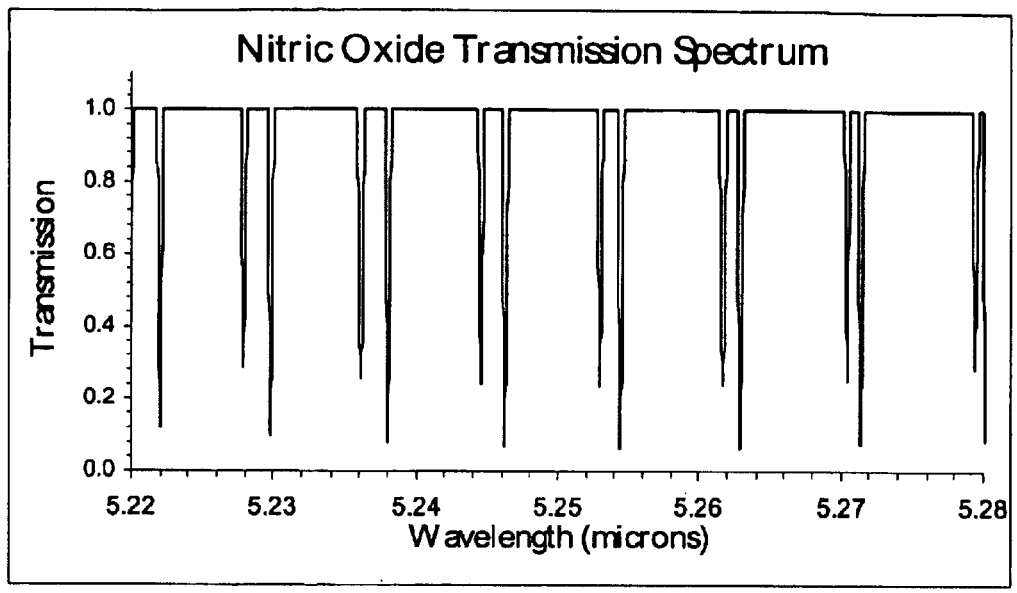
FIG. 3 show details of an absorption spectrum of the type that can be observed by the apparatus.
Figure 4:
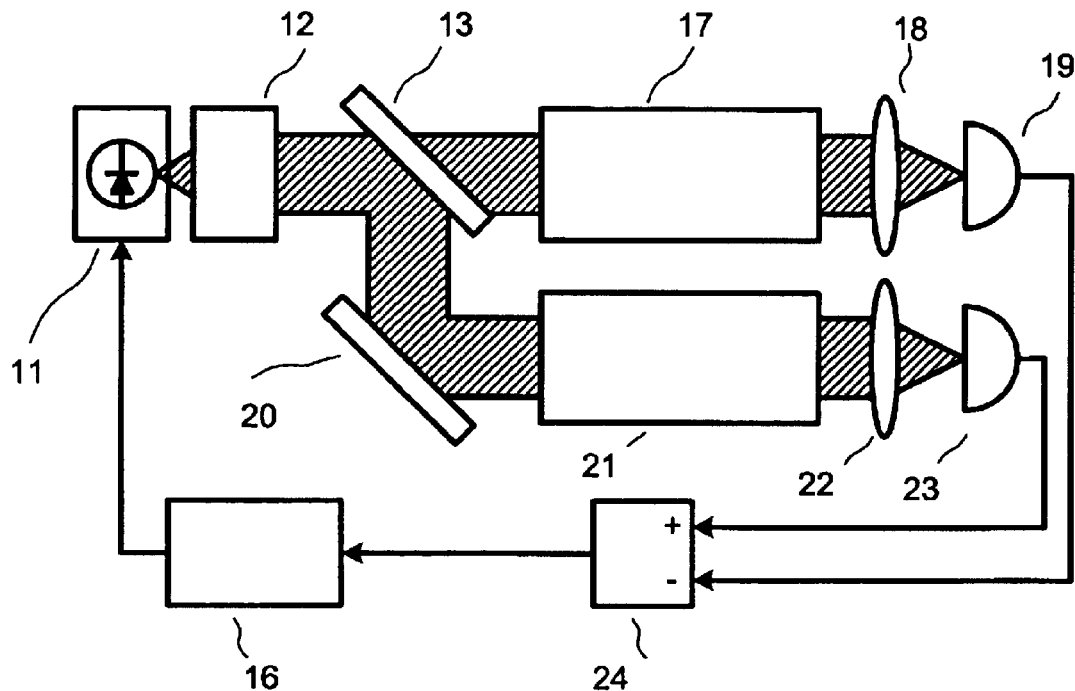
FIG. 4 is a schematic diagram of another prior art apparatus for measuring the absorption of a substance using light from a laser.

In the first mode of operation, the wavelength sensor 36 is operated so that it performs an integrating measurement over the duration of the pulse, determining a weighted center-of-mass measurement of the wavelength. This is done most easily by using analog electronics with response times that are slower than the pulse duration and faster than the time between successive pulses in wavelength sensor. Similarly, the monitor photodetector 41 measurement and the absorption detection photodetector 46 measurement are operated in the same weighted center-of-mass measurement averaging mode by setting the response times of amplifiers 42 and 47 to slower than the pulse duration and faster than the time between pulses. (Analog and amplifier electronics circuitry response times typically are determined by the combination of capacitance and resistance in the circuitry). Sets of three data points (the wavelength sensor data, the monitor photodiode data, and the absorption measurement data) are then recorded in electronics memory as representative samplings of the absorption of the sample at the different wavelengths. This provides a partial or complete wavelength scan of features of the absorption spectrum. If pulse-to-pulse variations of the wavelength are large, there may be enough variation to scan an entire spectral feature (see FIG. 3). Otherwise, the laser can be tuned in wavelength across the spectral feature to obtain needed data at other wavelengths.

In the second mode of operation, wavelength sensor 36, the monitor photodetector 41 (and accompanying amplifier 42) and the absorption measurement photodetector 46 (and accompanying amplifier 47) are configured to respond very quickly to wavelength changes in the laser pulse. In this mode, electronic signals from wavelength sensor 36, the monitor photodetector 41, and the absorption measurement photodetector 46 are recorded with the help of fast analog-to-digital converters or a fast digital oscilloscope. Similar to the case for the first mode of operation, sets of the three data points (the wavelength sensor data, the monitor photodiode data, and the absorption measurement data) are accumulated, but with the difference that the data corresponds to data for wavelength variations taking place during the pulse. This wavelength scan provides a partial or complete wavelength scan of features of the absorption spectrum and tuning to other wavelengths is implemented as needed.

Figure 7:
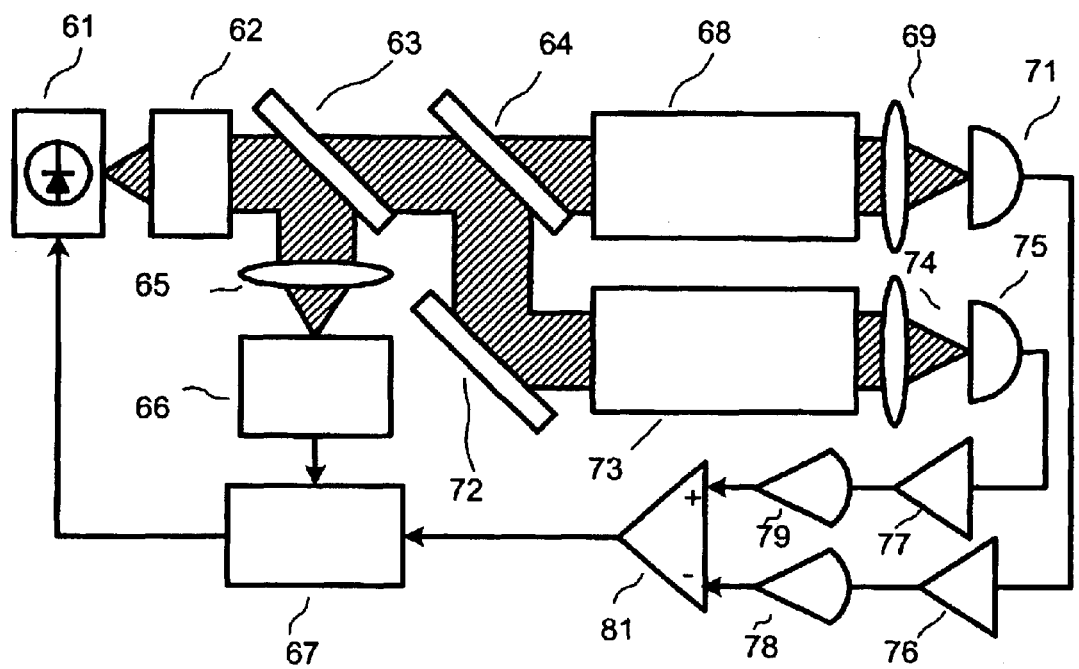
FIG. 7 is a schematic diagram of an absorption measurement device for measuring the concentration of a substance using light from a laser in accordance with another embodiment of the invention.

FIG. 7 illustrates another embodiment of the invention. Light from the laser source 61 is collimated into a beam by collimator 62 and split into three beams with the help of beamsplitters 63 and 64. The beam reflected from beamsplitter 63 goes through lens 65 to wavelength sensor 66 where the wavelength of the light from the laser is measured and the resulting measurement is sent to the electronics processor 67. The beam of light transmitted through beamsplitter 64 goes through cell 68 that contains the gas or substance to be measured and is focused with lens 69 onto photodetector 71. The beam reflected from beamsplitter 64 is deflected from mirror 72 and transmitted through a second cell 73 containing a known concentration of gas or the sample to be measured and is focused through lens 74 onto a second photodetector 75. Photocurrents from photodetectors 71 and 75 are sent through amplifiers 76 and 77 and logarithmic converters 78 and 79 and then subtracted from each other at subtractor 81 to provide a log difference signal that is a correlation of the absorption spectrum of the unknown sample and the known reference sample. Note, that the logarithm conversion steps can be performed digitally. Operation modes are similar to those described above for the embodiment schematized in FIG. 5.

If we describe the intensity of the beam of light from the laser source as having a wavelength and time dependence $I(\lambda,t)$ where $\lambda$ is the wavelength of the signal and t is the time, then the log difference signal $Spec(\lambda,t)$ that is a measurement of the absorption spectrum obtained by the apparatus diagrammed in FIG. 6 and described in the paragraph above is given by:

$$Spec(\lambda,t)=\log[I(\lambda,t) \cdot T_{sample}(\lambda) \cdot F_{sample}(\lambda) A_{sample}]-\log[I(\lambda,t) \cdot T_{ref}(\lambda) \cdot F_{ref}(\lambda) \cdot A_{ref}] \quad (1)$$

$$Spec(\lambda,t)=\log\{[I(\lambda,t) \cdot T_{sample}(\lambda) \cdot F_{sample}(\lambda) \cdot A_{sample}]/[I(\lambda,t) \cdot T_{ref}(\lambda) \cdot F_{ref}(\lambda) \cdot A_{ref}]\} \quad (2)$$

$$Spec(\lambda,t)=\log\{T_{sample}(\lambda) \cdot F_{sample}(\lambda) \cdot A_{sample}/T_{ref}(\lambda) \cdot F_{ref}(\lambda) \cdot A_{ref}\}. \quad (3)$$

Here, $T_{sample}(\lambda)$ is the transmission of the sample in the sample cell 68 as a function of wavelength and $T_{ref}(\lambda)$ is the transmission of the gas or substance in the reference cell 73 as a function of wavelength, $F_{sample}(\lambda)$ is the loss factor as a function of wavelength for the beam going through the sample cell 68 with nothing present and $F_{ref}(\lambda)$ is a loss factor as a function of wavelength for the beam going through the reference cell 73 with nothing present, and $A_{sample}$ and $A_{ref}$ are the gain of amplifiers 76 and 77 respectively. Because a log difference operation is equivalent to the logarithm of a ratio, the intensity $I(\lambda,t)$ cancels out (we have assumed for simplicity that the pulse is monochromatic with a time-varying wavelength) as shown in Equation (3). A further simplification can be obtained by assuming that $F_{sample}(\lambda)=F_{ref})$ and $A_{sample}=A_{ref}$, yielding $$\text{Spec}(\lambda,t)=\log[T_{sample}(\lambda)/T_{ref}(\lambda)]. \quad (4)$$

This particularly simple result is an intensity-independent correlation measurement over the wavelength range determined by wavelength sensor 66.

The advantage of this measurement method is threefold. First, an intensity independent correlation measurement is performed, and second, the dynamic range of the measurement is increased. Finally, the method is valid for spectroscopic and other lasers having pulsed (or continuous) operation where the wavelength varies during the pulse or there are pulse-by-pulse average wavelength variations. All of these are advantageous for measurement of the absorption spectrum of the sample material.

Thus, there has been described a laser absorption spectrometer for making measurements of absorption spectra which includes a wavelength sensor that can measure the average wavelength of pulses from a laser on a pulse-by-pulse basis and that can measure the internal wavelength variation of laser pulses. The laser absorption spectrometer can be used with pulsed lasers like the quantum cascade laser to perform sensitive measurements of the absorption spectra even when there is pulse-to-pulse variation of average wavelength and when there are internal changes in the wavelength of the pulses.

The foregoing descriptions of specific embodiments of the present invention are presented for the purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A spectrometer for making measurements of absorption spectra of a sample comprising:
    a source of a collimated beam of light,
    a rapid response wavelength sensor providing an output signal representative of the wavelength of a light beam,
    a monitor photodetector for receiving a light beam and providing an output signal representative of its intensity,
    beam splitting means for receiving the beam and transmitting parts to the wavelength sensor, the monitor photodetector and the sample,
    a sample photodetector for receiving the portion of the beam after it has traveled through the sample and providing an output signal representative of its intensity, and
    electronics for receiving the wavelength sensor output signal, the monitor photodetector output signal and the sample photodetector output signal and processing the signals to produce an absorption spectrum.

2. A spectrometer as in claim 1 in which the source of collimated light beam is a laser and the means for collimating the laser beam.

3. A spectrometer as in claim 2 in which said laser is tunable and said electronic means provides a tuning signal to said laser.

4. A spectrometer as in claim 2 in which said laser is a pulsed laser.

5. A spectrometer as in claim 2 in which said laser is a quantum cascade laser.

6. A spectrometer as in claims 1 or 2 which includes log circuits which receives the signals from the monitor photodetector and the sample photodetector which are processed by said log circuits to provide the log of said signals and the logs are then subtracted.

7. A spectrometer as in claims 1 or 2 including a cell for holding trace gases or other samples whose absorption spectrum is to be measured.

8. An absorption spectrometer for measuring the absorption of a sample comprising;
    a laser for emitting light,
    collimating means for receiving the laser light and forming a light beam,
    a sample absorption cell for holding a trace gas or other substance whose absorption spectrum is to be measured,
    a reference cell to hold trace gas or other substance whose absorption spectrum is to be compared with that in the sample absorption cell,
    a rapid response wavelength sensor for measuring the wavelength of the light beam and providing a wavelength output signal,
    means for transmitting part of the beam to the wavelength sensor, part to the sample absorption cell and part to the reference absorption cell,
    photodetectors for receiving the beam passing through the sample and reference cells and providing output signals representative of the intensity of the transmitted beams, and
    electronics for receiving the wavelength sensor signal and the photodetector signals and processing the signals to provide an absorption spectrum.

9. A spectrometer as in claim 8 in which said laser is a pulsed laser.

10. A spectrometer as in claim 8 in which said laser is a quantum cascade laser.

11. A spectrometer as in claim 8 including photodetector signal processing electronics which amplify the signals from the photodetectors.

12. A spectrometer as in claim 8 in which said processing electronics include log circuits that receive the output signals and provide the log of such signals and then subtract the resulting logs to produce a difference signal.

* * * * *